United States Patent
Bui

(10) Patent No.: US 6,986,753 B2
(45) Date of Patent: Jan. 17, 2006

(54) CONSTANT OCULAR PRESSURE ACTIVE INFUSION SYSTEM

(75) Inventor: Hai Bui, Fountain Valley, CA (US)

(73) Assignee: Buivision, Fountain Valley, CA (US)

( * ) Notice: Subject to any disclaimer, the term of this patent is extended or adjusted under 35 U.S.C. 154(b) by 0 days.

(21) Appl. No.: 09/316,851

(22) Filed: May 21, 1999

(65) Prior Publication Data

US 2002/0019607 A1    Feb. 14, 2002

Related U.S. Application Data

(60) Provisional application No. 60/086,283, filed on May 21, 1998.

(51) Int. Cl.
*A61M 31/00* (2006.01)
*A61M 1/00* (2006.01)

(52) U.S. Cl. .......................... 604/31; 604/67; 604/151

(58) Field of Classification Search .................. 604/22, 604/27, 28, 30, 31, 35, 43, 67, 151, 131, 604/54, 246, 23
See application file for complete search history.

(56) References Cited

U.S. PATENT DOCUMENTS

| | | |
|---|---|---|
| 3,812,855 A | 5/1974 | Banko |
| 3,920,014 A | 11/1975 | Banko |
| 3,955,574 A | 5/1976 | Rubinstein |
| 4,007,742 A | 2/1977 | Banko |
| 4,014,333 A | 3/1977 | McIntyre |
| 4,052,987 A | 10/1977 | Wuchinich et al. |
| 4,117,843 A | 10/1978 | Banko |
| 4,191,204 A | 3/1980 | Nehring |
| 4,324,243 A | 4/1982 | Helfgott et al. |
| 4,423,727 A | 1/1984 | Widran et al. |
| 4,508,532 A | 4/1985 | Drews et al. |
| 4,537,561 A | 8/1985 | Xanthopoulos |
| 4,544,336 A | 10/1985 | Faeser et al. |
| 4,626,248 A | 12/1986 | Scheller |
| 4,758,220 A | 7/1988 | Sundblom et al. |
| 4,770,654 A | 9/1988 | Rogers et al. |
| 4,790,816 A | 12/1988 | Sundblom et al. |
| 4,810,242 A | 3/1989 | Sundblom et al. |
| 4,933,843 A | 6/1990 | Scheller et al. |
| 4,989,590 A | 2/1991 | Baum et al. |
| 5,106,367 A | 4/1992 | Ureche et al. |
| 5,167,620 A | 12/1992 | Ureche et al. |
| 5,279,547 A | 1/1994 | Costin |

(Continued)

FOREIGN PATENT DOCUMENTS

WO    WO 93/18802    *    2/1993

(Continued)

*Primary Examiner*—Nicholas D. Lucchesi
*Assistant Examiner*—Matthew F. DeSanto
(74) *Attorney, Agent, or Firm*—Blakely Sokoloff Taylor & Zafman, LLP

(57) ABSTRACT

An irrigation system for a medical device. The irrigation system may include a pump that can pump irrigation fluid from a reservoir through an irrigation line. The system may further have a controller coupled to the pump and an accumulator pressure sensor that senses the pressure of the irrigation line. The controller can vary the speed of the pump in response to a change in the line pressure to control the irrigation line pressure. Additionally, the controller can monitor the fluidic resistance of the system by determining the pump speed and corresponding flowrate of the pump. The controller can provide one or more safety output signals if the fluidic resistance exceeds a threshold value(s).

28 Claims, 2 Drawing Sheets

U.S. PATENT DOCUMENTS

| | | |
|---|---|---|
| 5,328,456 A | 7/1994 | Horiguchi et al. |
| 5,429,601 A | 7/1995 | Conley et al. |
| 5,562,612 A | 10/1996 | Fox |
| 5,580,347 A | 12/1996 | Reimels |
| 5,609,576 A * | 3/1997 | Voss et al. .................... 604/67 |
| 5,700,240 A * | 12/1997 | Barwick et al. .............. 604/22 |
| 5,716,342 A | 2/1998 | Dumbraveanu et al. |
| 5,733,256 A * | 3/1998 | Costin ......................... 604/22 |
| 5,830,176 A | 11/1998 | Mackool |
| 5,857,485 A | 1/1999 | Perkins et al. |

FOREIGN PATENT DOCUMENTS

| | | | |
|---|---|---|---|
| WO | WO 93/18802 | * | 9/1993 |
| WO | WO9318802 | * | 9/1993 |

* cited by examiner

CONSTANT OCULAR PRESSURE ACTIVE INFUSION SYSTEM

This application claims benefit of Ser. No. 60/086,283, filed May 21, 1998.

BACKGROUND OF THE INVENTION

1. Field of the Invention

The present invention relates to an irrigation system for a medical device such as a phacoemulsification handpiece.

2. Background Information

The lens of an eye can be removed in a procedure commonly referred to as phacoemulsification ("phaco"). In a phaco procedure an ultrasonically driven tip is inserted through a small incision in the cornea and used to emulsify the lens. The tip extends from a handpiece that is held by a surgeon. The tip is coupled to an irrigation system that supplies an irrigation fluid to the surgical site. The tip is also coupled to an aspiration system that aspirates the irrigation fluid and the emulsified lens. The irrigation fluid provides a medium to remove the emulsified lens. Additionally, the irrigation fluid provides a medium to transfer heat generated by the ultrasonically driven tip.

When performing a phaco procedure emulsified lens tissue may occlude the aspiration line. The occlusion may increase the downstream vacuum pressure of the aspiration line. If the occlusion becomes dislodged the cornea will be exposed to the increased vacuum pressure. This large instantaneous vacuum pressure may cause the cornea to collapse. There have been developed various devices and systems for preventing a cornea collapse due to an occlusion in the aspiration line. For example, U.S. Pat. No. 5,106,367 issued to Ureche, et al. discloses a vacuum surge suppressor that limits the transient flow during a vacuum surge by increasing the resistance of the aspiration line.

Most phaco systems address the issue of occlusion and control of intraocular pressure with devices, sensors etc. in the aspiration system. The aspiration system is downstream from the eye. The control of pressure and flowrate in the eye is therefore somewhat limited. Such a system is similar to controlling the flow of water through a stream with a dam located at the end of the stream. Any input from a downstream dam will have a delayed and possibly attenuated effect on the upstream conditions. It would be desirable to integrate control and safety features in the upstream irrigation systems.

U.S. Pat. Nos. 3,812,855 and 3,920,014 issued to Banko disclose an irrigation system that contains a plurality of solenoid actuated valves which control the flow of an irrigation fluid to a surgical site. Each valve may have an adjustable needle to vary the flowrate and corresponding pressure of the irrigation fluid. The Banko system provides no intelligence as to an occluded condition or any type of feedback loop that can be used to control the intraocular pressure. It would be desirable to provide an irrigation system that can control the intraocular pressure and provide various safety features for an ophthalmic surgical procedure.

SUMMARY OF THE INVENTION

One embodiment of the present invention is an irrigation system for a medical device. The irrigation system may include a pump that can pump irrigation fluid from a reservoir through an irrigation line. The system may further have a controller coupled to the pump and an accumulator pressure sensor that senses the pressure of the irrigation line. The controller can vary the speed of the pump in response to a change in the line pressure to control the irrigation line pressure. Additionally, the controller can monitor the fluidic resistance of the system by determining the pump speed and corresponding flowrate of the pump. The controller can provide one or more safety output signals if the fluidic resistance exceeds a threshold value(s).

DETAILED DESCRIPTION

Figure 1:
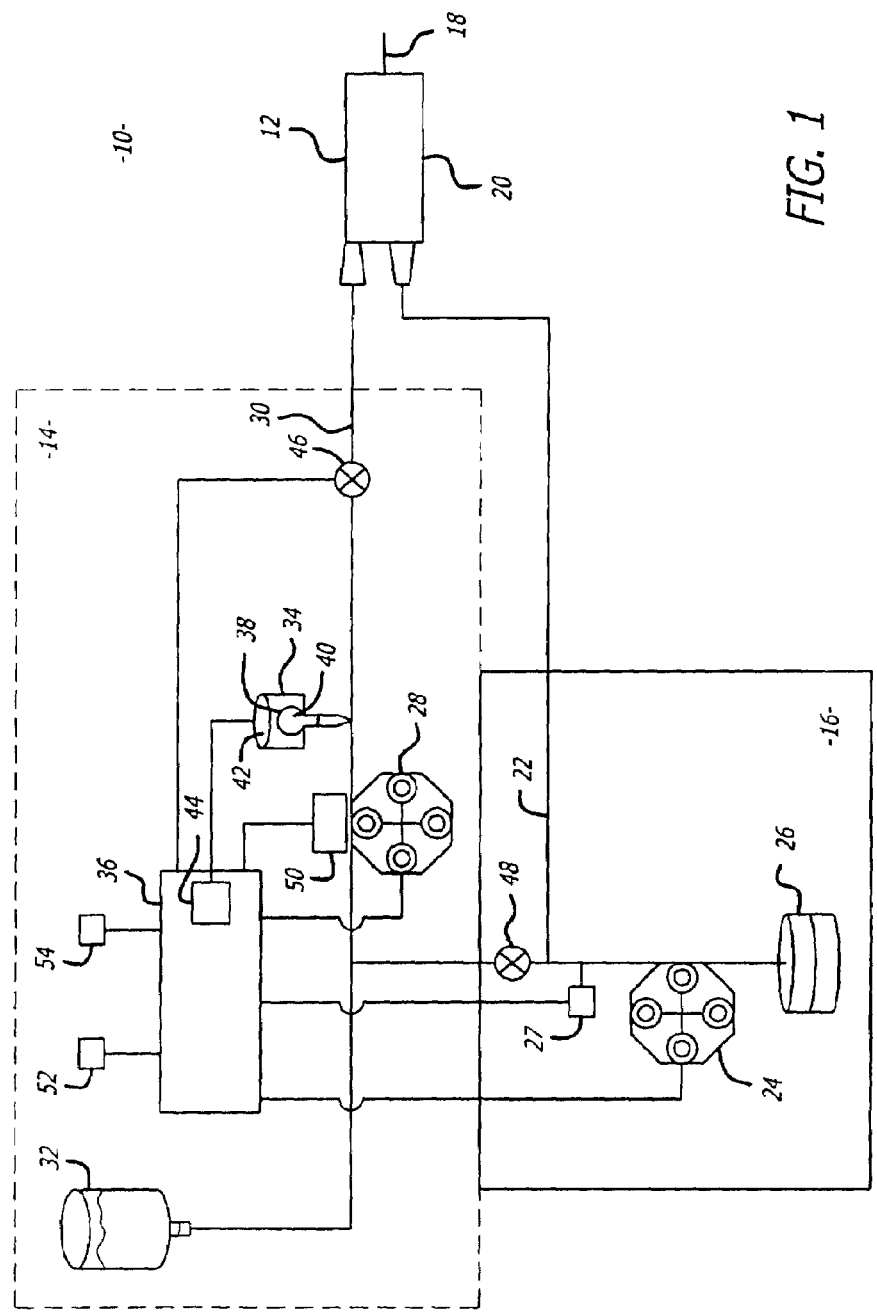
FIG. 1 is a schematic of an embodiment of a medical system of the present invention.
Figure 2:
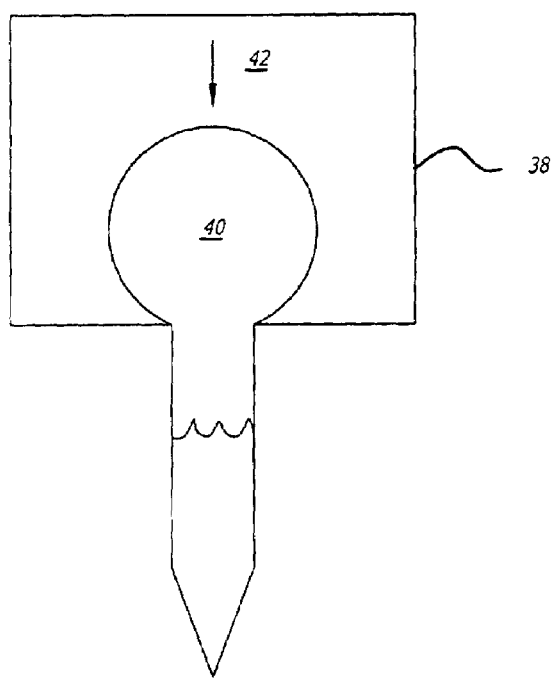
FIG. 2 is an exemplary embodiment of the accumulator of FIG. 1.

Referring to the drawings more particularly by reference numbers, FIG. 1 shows an embodiment of a medical system 10 of the present invention. The system 10 may include a medical device 12 that is coupled to an irrigation system 14 and an aspiration system 16. The medical device 12 may include an ultrasonically driven tip 18 that extends from a handpiece 20. The handpiece 20 is typically held by a surgeon who inserts the tip 18 through an incision in a cornea (not shown). The irrigation system 14 provides an irrigation fluid to the tip 18 and the surgical site. The aspiration system 16 removes the irrigation fluid and any detached tissue from the surgical site. Although a phaco handpiece is shown and described, it is to be understood that the system 10 may contain another type of medical device such as a guillotine cutter.

The aspiration system 16 may include an aspiration line 22 that is coupled to an aspiration pump 24 and the tip 18 of the medical device 12. The pump 24 may pull irrigation fluid and tissue from the surgical site to a depository 26. By way of example, the aspiration pump 24 may be a non-invasive peristaltic pump. The aspiration system 16 may include a pressure sensor 27 that senses the pressure of the aspiration line 22.

The irrigation system 14 may include an irrigation pump 28 that is coupled to an irrigation line 30 and an irrigation fluid reservoir 32. The reservoir 32 may be an IV bottle full of irrigation fluid as is known in the art. The irrigation pump 28 may be a non-invasive peristaltic pump that generates a flow of irrigation fluid through the line 30 from the reservoir 32 to the medical device 12.

The irrigation system 14 may further have an accumulator 34 coupled to the irrigation line 30. The accumulator 34 may be coupled to a controller 36. The controller 36 may also be coupled to the pump 28. The controller 36 may include a microprocessor, memory, etc. that can receive input signals, process the signals in accordance with a software routine(s) and provide output signals.

The accumulator 34 may include a flexible membrane 38 that separates a first chamber 40 from a second chamber 42. The first chamber 40 is in fluid communication with the irrigation line 30. The second chamber 42 is in fluid communication with a pressure transducer 44 of the controller 36.

During normal operation, the membrane 38 will deflect with variations in pressure of the irrigation line 30 and the first chamber 40. Deflection of the membrane 38 will change the volume of the second chamber 42 and the corresponding pressure therein. The change in pressure within the irrigation line 30 is sensed by the pressure transducer 44 of the controller 36.

The accumulator 34 provides multiple functions. The first chamber 40 provides a reservoir of pressurized fluid for the system and functions as a fluidic capacitor that can maintain the intraocular pressure of the eye. The flexible membrane 38 and first chamber 40 can also filter pressure pulsations created by the pump 28. Additionally, the flexible membrane 38 provides a non-invasive means for sensing the pressure within the irrigation line 30. The system may include an accumulator (not shown) that provides additional capacitance for the second chamber 42. The additional accumulator may reduce the sensitivity of the pressure sensor 34 and allow greater volume of irrigation fluid to be stored in the first chamber 40.

The irrigation system 14 may include a valve 46 that can be switched by the controller 36 between an on position and an off position to control the flow of irrigation fluid through the irrigation line 30. The system 10 may also have a valve 48 that couples the irrigation system 14 to the aspiration system 16. The valve 48 can be opened to reflux or vent the aspiration line 30.

In operation, the controller 36 may receive an input signal from the transducer 44 that corresponds to the pressure within the irrigation line 30. The controller 36 may compare the actual pressure signal with a desired pressure signal. If the actual pressure deviates from the desired pressure the controller 36 may provide an output signal(s) to vary the speed of the pump 28. To prevent a constant switching of the pump 28 the controller 36 may determine whether the actual pressure is within a desired range of pressures. If the actual pressure is within the desired range the controller 36 may not vary the speed of the pump 28. If the actual pressure is outside the desired range the controller 36 can vary the pump speed, accordingly.

By way of example, if the valve 46 is open and the actual pressure is greater than the desired range, the controller 36 can decrease the speed of the pump 28 to reduce the irrigation pressure. Likewise, if the actual pressure is less than the desired range the controller 36 can increase the speed of the pump 28. If the valve 46 is closed the irrigation pressure can be decreased by reversing the direction of the pump 28 to pump fluid out of the accumulator 34. The controller 36, accumulator 34 and pump 28 can thus be used as a closed loop feedback system to control the intraocular pressure of an eye during a surgical procedure.

The irrigation system 14 may have a speed sensor 50 that can provide a feedback signal to the controller 36 which corresponds to the speed of the pump 28. The speed sensor 50 may be an optical encoder (not shown) and accompanying circuitry coupled to the output shaft of the pump motor (not shown). Pumps 28 are positive displacement type pumps. In a normal operating range the flowrate generated by the pump 28 is linearly proportional to the pump speed. The controller 36 can thus determine the flowrate from the speed of the pump 28 with one or more relatively simple calculations.

The controller 36 can calculate the volume of fluid pumped through the irrigation line 30 by multiplying the flowrate with the pumping time. The controller 36 can predict when the reservoir 32 is being depleted by comparing the calculated fluid volume with a threshold value. The threshold value may correspond to a predetermined volume of the reservoir 32. When the calculated volume is greater than the threshold value the controller 36 can activate a visual and/or audio indicator 52 to warn the operator to replace the reservoir 32.

Additionally, the ability to sense the instantaneous irrigation flowrate enables the controller 36 to maintain a constant intraocular pressure by compensating for the pressure drop in the irrigation circuit. With a known irrigation source resistance, the controller 36 can easily calculate and compensate for the pressure loss using the basic fluid equation: Pressure=Flow×Resistance. The irrigation source resistance can be determined in the design phase using both theoretical and emperical methods. This typical value can be stored in the controller 36 as constant. However, for better results, the control system can accurately determine the irrigation resistance for each specific setup by measuring the flowrate at a specific pressure with irrigation free flow and calculate the resistance.

By sensing the flowrate the controller 36 can also determine whether there is an occlusion in the aspiration system 16. An occlusion will increase the fluidic resistance of the entire system. The controller 36 can calculate the fluidic resistance by dividing the differential pressure across the system by the flowrate. The calculated actual fluidic resistance can be compared to a threshold resistance value. If the actual resistance is greater than the threshold the controller 36 may activate a visual and/or audio indicator 54 to warn the surgeon that an occlusion may exist in the system.

If the actual resistance is greater than the threshold value, the controller 36 may also change the speed of the aspiration pump 24 to alter the rate of vacuum rise within the aspiration line 22. The controller 36 may reduce or terminate the power to the medical device 12 to prevent undesirable heating of tissue by the ultrasonically driven tip 18. Power reduction may be accomplish by decreasing the power level and or applying the power in an intermittent manner (i.e. pulse, burst, etc.). The reduction or termination of power may correspond to different resistance thresholds. By way of example, when the actual resistance exceeds a first threshold the controller 36 may reduce power to the medical device 12. When the actual resistance is greater than a higher threshold the controller 36 may actually turn the device off.

The threshold resistance value(s) can be normalized with the actual resistance of the system by either calculating the system resistance, or measuring the resistance when the system is set up and the device is inserted into a test chamber. The system resistance can be calculated by allowing irrigation fluid to flow through the irrigation line, test chamber, and aspiration line, and then determining the resistance by dividing the sensed differential pressure by the measured flowrate. The flowrate can be determined from the speed of the pump 28. The differential pressure can be determined from the pressures sensed by sensor] 27 and accumulator 34.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An irrigation system for a medical device, comprising:
   an irrigation line;
   a valve to control a flow of fluid through said irrigation line;
   an irrigation reservoir providing fluid to the irrigation line, the irrigation reservoir operating as a first source of fluid for the medical device;
   a pump coupled to said irrigation line;
   an accumulator operating as a secondary source of fluid for the medical device, said accumulator including a first chamber, a second chamber, and a flexible membrane that separates said first chamber from said second chamber and deflects in response to a change in an amount of fluid pressure in the irrigation line, said first chamber of said accumulator providing a reservoir for pressurized fluid and supplying said pressurized fluid to said irrigation line in response to reduced speed of said pump and without adjustment of said valve; and, a controller including a pressure transducer in fluid communication with said second chamber to detect a change of fluid pressure in said second chamber caused by the deflection of the flexible membrane and to adjust said valve and control a flow rate of fluid passing through said irrigation line to counteract the change in the amount of fluid pressure in the irrigation line by varying a speed of said pump.

2. The irrigation system of claim 1, wherein said controller can determine a flowrate generated by said pump.

3. The irrigation system of claim 2, wherein said controller determines an actual fluidic resistance from the flowrate and provides an output signal if the actual fluidic resistance is greater than a threshold value.

4. The irrigation system of claim 2, wherein said controller determines an actual volume of irrigation fluid pumped by said pump from the flowrate and provides an output signal if the actual volume of irrigation fluid is greater than a threshold value.

5. The irrigation system of claim 1, further comprising a valve coupled to said irrigation line and said controller.

6. The irrigation system of claim 1, wherein said controller activates an indicator to provide a warning to replace said irrigation reservoir.

7. The irrigation system of claim 1, wherein said controller varies said pump speed in response to a variation in the irrigation line pressure sensed by said pressure transducer that rises above a desired range of pressures.

8. A medical system, comprising:
an irrigation system that includes
an irrigation reservoir storing fluid,
an irrigation pump that is coupled to said irrigation reservoir to control an output
rate of the fluid from the irrigation reservoir,
an irrigation line coupled to said irrigation reservoir,
an accumulator providing fluid different than the fluid provided by the irrigation reservoir as a secondary source, said accumulator being directed coupled to said irrigation line and including a first chamber in fluid communication with said irrigation line, a second chamber, and a flexible membrane that separates said first chamber from said second chamber and deflects in response to a change in an amount of fluid pressure in the irrigation line, said first chamber of said accumulator providing a reservoir of pressurized fluid and supplying said pressurized fluid to said irrigation line in response to reduced speed of said pump; and,
a controller including a pressure transducer in fluid communication with said second chamber and to control the pressure within said irrigation line through monitoring a change of fluid pressure within said second chamber of said accumulator; and
an aspiration system that includes
an aspiration pump,
an aspiration line coupled to said aspiration pump, and
an aspiration pressure sensor that senses a vacuum pressure within said aspiration line.

9. The medical system of claim 8, wherein said controller can determine a flowrate generated by said irrigation pump.

10. The medical system of claim 9, wherein said controller determines an actual fluidic resistance from the flowrate and provides an output signal if the actual fluidic resistance is greater tan a threshold value.

11. The medical system of claim 10, wherein said controller provides an output signal that is used to control power of a medical device that is coupled to said irrigation line and said aspiration line if the actual fluidic resistance is greater than a device threshold value.

12. The medical system of claim 10, wherein said controller changes a speed of said aspiration pump if the actual fluidic resistance is greater than a threshold resistance value.

13. The medical system of claim 9, wherein said controller determines an actual volume of irrigation fluid pumped by said irrigation pump from the flowrate and provides an output signal if the actual volume of irrigation fluid is greater than a threshold value.

14. The medical system of claim 8, wherein said controller maintains an intraocular pressure by varying a speed of said irrigation pump and a flowrate through said irrigation line.

15. The medical system of claim 14, wherein said controller varies said speed of said irrigation pump in response to a variation in fluid pressure in said first chamber of said accumulator as sensed by said pressure transducer.

16. An apparatus comprising:
an irrigation pump;
an irrigation line controlled in the irrigation pump and providing a first fluid path;
a fluid reservoir to supply a fluid to the irrigation line over the first fluid path;
a first pressure sensor in fluid communication with the irrigation line; and
a first accumulator located between the irrigation line and the first pressure sensor and providing a second fluid path that is separate from the first fluid path and feeds into the first fluid path, the first accumulator including a first chamber in fluid communication with the irrigation line temporarily to provide stored pressurized fluid in addition to the fluid supplied by the fluid reservoir in response to dislodgment of an occlusion of an aspiration line after the occlusion has already caused a substantially reduced speed of the irrigation pump, a second chamber in fluid communication with the first pressure sensor and a flexible membrane which separates the first and the second chamber.

17. The apparatus of claim 16 further comprising:
an aspiration line;
a second pressure sensor in fluid communication with the aspiration line;
an aspiration pump in fluid communication with the aspiration line; and,
a controller coupled with the first and the second pressure sensors to sense a differential pressure between the irrigation line and the aspiration line and to vary a speed of the irrigation pump in efforts to maintain a flow rate in the irrigation line substantially in proportion to the flow rate in the aspiration line.

18. The apparatus of claim 17, wherein the controller is further to determine that an occlusion of the aspiration line has occurred if the differential pressure increases.

19. The apparatus of claim 16 wherein the first accumulator is sized to maintain an intraocular pressure of an eye into which the medical device is to be inserted.

20. An irrigation system for a medical device, comprising:
a pump;
an irrigation line coupled to said pump;
a controller that varies a speed of said pump to adjust a flowrate of fluid passing through said irrigation line over a first fluid path; and
an accumulator including (i) a first chamber operating as a reservoir to store pressurized fluid separately from fluid passing through said irrigation line, (ii) a second chamber in fluid communication with said controller, and (iii) a flexible membrane that separates said first chamber from said second chamber, said accumulator provides said pressurized fluid from said first chamber to said irrigation line over a second fluid path separate and distinct from the first fluid path, said pressurized fluid being provided in addition to other fluid passing through said irrigation line to maintain intraocular pressure of an eye.

21. The irrigation system of claim 20 further comprising an irrigation reservoir coupled to said irrigation line.

22. The irrigation system of claim 21, wherein said pressurized fluid from said first chamber is provided to said irrigation line to mitigate transit latency of fluid from said irrigation reservoir.

23. The irrigation system of claim 21, wherein said controller activates an indicator to provide a warning to replace said irrigation reservoir.

24. The irrigation system of claim 20, wherein said flexible membrane of said accumulator is deflected in response to a change in fluid pressure in said irrigation line and causes a change in fluid pressure in said second chamber.

25. The irrigation system of claim 24, wherein said controller including a pressure transducer in fluid communication with said second chamber to detect the change of fluid pressure in said second chamber caused by deflection of said flexible membrane and to adjust a flowrate of said fluid passing through said irrigation line to counteract the change in fluid pressure in said irrigation line by varying the speed of said pump.

26. An irrigation system for a medical device comprising:
an irrigation line;
a valve to control a flow of fluid through said irrigation line;
a pump coupled to said irrigation line to control a flow of fluid through said irrigation line;
an accumulator including a first chamber, a second chamber, and a flexible membrane that separates said first chamber from said second chamber and deflects in response to a change in an amount of fluid pressure in said irrigation line, said first chamber of said accumulator operating as a reservoir to store fluid separately from fluid passing through said irrigation line, said fluid stored by said accumulator is provided from said first chamber to said irrigation line separately from said fluid flowing through said irrigation line under control by said pump and without adjustment of said valve; and,
a controller including a pressure transducer in fluid communication with said second chamber, said controller to detect a change of fluid pressure in said second chamber caused by the deflection of the flexible membrane and to adjust a flowrate through said irrigation line to counteract a change in the amount of fluid pressure in said irrigation line by varying a speed of said pump.

27. The irrigation system of claim 26 further comprising an irrigation reservoir coupled to said irrigation line.

28. The irrigation system of claim 27, wherein said fluid from said first chamber is provided to said irrigation line to account for a delay of additional fluid being provided from said irrigation reservoir.

* * * * *